(12) United States Patent
Bessard et al.

(10) Patent No.: US 7,009,058 B1
(45) Date of Patent: Mar. 7, 2006

(54) METHOD FOR PREPARING PYRIDINE-2,3-DICARBOXYLIC ACID ESTERS

(75) Inventors: Yves Bessard, Sierre (CH); Gerhard Stucky, Brig-Glis (CH); Jean-Paul Roduit, Grone (CH)

(73) Assignee: Lonza AG, Gampel/Valais (CH)

( * ) Notice: Subject to any disclaimer, the term of this patent is extended or adjusted under 35 U.S.C. 154(b) by 0 days.

(21) Appl. No.: 09/568,993

(22) Filed: May 11, 2000

Related U.S. Application Data

(63) Continuation of application No. 09/257,932, filed on Feb. 26, 1999, now abandoned, which is a continuation-in-part of application No. 08/890,767, filed on Jul. 11, 1997, now abandoned.

(30) Foreign Application Priority Data

Jul. 23, 1996 (CH) ..................................... 1840/96

(51) Int. Cl.
*C07D 213/80* (2006.01)
*C07D 213/803* (2006.01)

(52) U.S. Cl. ..................... 546/319; 546/296; 546/299; 546/321

(58) Field of Classification Search ............... 546/296, 546/299, 319, 321
See application file for complete search history.

(56) References Cited

U.S. PATENT DOCUMENTS

| | | | |
|---|---|---|---|
| 5,142,057 A | 8/1992 | Suto et al. | |
| 5,166,352 A | 11/1992 | Allphin | |
| 5,288,866 A | 2/1994 | Strong | |
| 5,296,601 A | 3/1994 | Suto et al. | |
| 5,925,765 A * | 7/1999 | Bessard et al. ............. | 546/327 |

FOREIGN PATENT DOCUMENTS

| | | |
|---|---|---|
| CH | 664754 | 3/1988 |
| DE | 4207604 | 9/1992 |
| EP | 0282266 * | 9/1988 |
| EP | 0461401 | 12/1991 |
| EP | 0820987 A1 * | 8/1997 |

OTHER PUBLICATIONS

Chemical Abstracts, CA Reference 132:64145, "Preparation of pyridinecarboxylates from chloropyridines by palladium-catalyzed alkoxycarbonylation" 2000, p. 682-683.*
Bessard, et al., "Selective Alkoxycarbonylation of 2, 3-Dichloropyridines", Tetrahedron 55 (1999) pp. 393-404.*
CA 126:212013, "Regiospecific carboalkoxylation of 2,5-dibromopyridine,", Chambers, p. 1, Synthetic Communications, 27 (3), 515-520.*
Chemical Abstracts, vol. 125, No. 3, 33323 k, (Jul. 15, 1996).
Paquette, L. A., Encyclopedia of Reagents for Organic Synthesis, vol. 4 (1995), pp. 2769-2771.

* cited by examiner

*Primary Examiner*—Patricia L. Morris
(74) *Attorney, Agent, or Firm*—Fisher Christen & Sabol

(57) ABSTRACT

A method for preparing pyridine-2,3-dicarboxylic acid esters of the general formula:

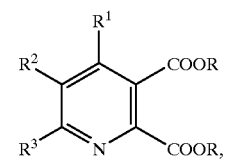

I wherein R is $C_{1-6}$-alkyl, $C_{3-6}$-cycloalkyl, aryl or arylalkyl, and $R^1$ to $R^3$, independently of one another, represent hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl. These esters are obtained from the corresponding 2,3-dichloropyridine, the corresponding alcohol ROH and carbon monoxide in the presence of a palladium-diphosphine complex and a weak base. Pyridine-2,3-dicarboxylic acid esters are herbicides or intermediates for the preparation of herbicides.

28 Claims, No Drawings

METHOD FOR PREPARING PYRIDINE-2,3-DICARBOXYLIC ACID ESTERS

This application is a continuation of U.S. application Ser. No. 09/257,938, filed on Feb. 26, 1999, abandoned, that is a continuation-in-part of U.S. application Ser. No. 08/890,767, filed on Jul. 11, 1997, abandoned, that has priority benefit of Switzerland Patent Application No. 1840/96, filed on Jul. 23, 1996.

BACKGROUND OF THE INVENTION

1. Field of the Invention

The invention relates to a method for preparing substituted diesters of pyridine-2,3-dicarboxylic acids by reacting 2,3-dichloropyridines with carbon monoxide and an alcohol in the presence of a catalyst and a base. The diesters which can be prepared according to the invention have the general formula:

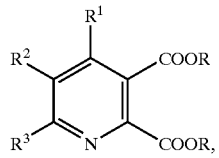

wherein:
R represents $C_{1-6}$-alkyl, $C_{3-6}$-cycloakyl, aryl or arylalkyl, and
$R^1$ to $R^3$, independently of one another, represent hydrogen, $C_{1-6}$-alkyl, fluorinated $C_{1-6}$-alkyl, $C_{1-6}$-alkoxy, $(C_{1-6}$-alkoxy)-$C_{1-6}$-alkyl or $(C_{1-6}$-alkoxy)carbonyl.

2. Background Art

Numerous compounds having this structure are important herbicides or synthesis building blocks for the preparation of herbicides (U.S. Pat. No. 5,288,866). The synthesis of these known compounds usually starts from the corresponding carboxylic acids or carboxylic acid derivatives (acid chlorides, nitrites). These, however, are often not readily accessible and, therefore, are expensive.

A further method (U.S. Pat. No. 5,296,601) for preparing diethyl pyridine-2,3-dicarboxylates starts from 2,3-dichloropyridine which is reacted with ethanol and carbon monoxide in the presence of a palladium complex, which contains 1,4-bis(diphenylphosphino)butane as ligands, and sodium carbonate as the base to give the diester. However, the yield is so low (<3 percent) that an industrial application of the method would be entirely uneconomical.

BROAD DESCRIPTION OF THE INVENTION

An object of the present invention is to provide a method which starts from readily accessible starting materials and gives high yields. Other objects and advantages of the invention are set out herein or are obvious herefrom to one skilled in the art.

The objects and advantages of the invention are achieved by the method and the compound of the invention.

The invention involves a method for preparing pyridine-2,3-dicarboxylic acid esters of the general formula:

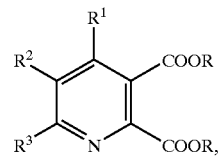

wherein R is $C_{1-6}$-alkyl, $C_{3-6}$-cycloalkyl, aryl or arylalkyl, and $R^1$ to $R^3$, independently of one another, represent hydrogen, $C_{1-6}$-alkyl, fluorinated $C_{1-6}$-alkyl, $C_{1-6}$-alkoxy, $(C_{1-6}$-alkoxy)-$C_{1-6}$-alkyl or $(C_{1-6}$-alkoxy)carbonyl. It was found that 2,3-dichloropyridines of the general formula:

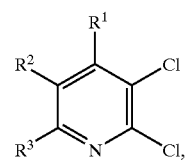

wherein $R^1$ to $R^3$ have the above-mentioned meanings, react directly with carbon monoxide and an alcohol of the general formula:

R—OH    III, wherein R has the above-mentioned meaning, in the presence of a base, with good yield, to give the desired products (I) if, as a catalyst, a complex of palladium with a diphosphine of the general formula:

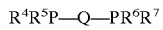

$R^4R^5P$—Q—$PR^6R^7$    IV, wherein $R^4$ to $R^7$, independently of one another, represent optionally substituted phenyl, $C_{1-6}$-alkyl or $C_{3-6}$-cycloalkyl, and Q represents a 1,1'-ferrocenediyl group or a group of the formula —$[CH_2]_n$, wherein n is 3 or 4, is present and the base used is a weak base from the group consisting of the alkali metal salts of lower carboxylic acids, the alkaline earth metal salts of lower carboxylic acids, the alkali metal hydrogen carbonates, the alkaline earth metal hydrogen carbonates, the alkali metal (di)hydrogen phosphates or the alkaline earth metal (di)hydrogen phosphates or generally a base having a $pK_a$ value of from 4 to 9.

Herein, the term $C_{1-6}$-alkyl should be understood as referring to any linear or branched primary, secondary or tertiary alkyl groups having up to 6 carbon atoms. Correspondingly, the terms $C_{1-6}$-alkoxy and ($C_{1-6}$-alkoxy)carbonyl should be understood as referring to the ether and ester functions composed of $C_{1-6}$-alkyl and oxygen, or oxygen and carbonyl, respectively, and analogously ($C_{1-6}$-alkoxy)-$C_{1-6}$-alkyl to the alkoxyalkyl groups formed by a hydrogen atom in $C_{1-6}$-alkyl being replaced by $C_{1-6}$-alkoxy, for example, methoxymethyl or ethoxymethyl.

Herein, the term aryl should be understood to refer, in particular, to mono- or polycyclic systems, for example, phenyl, naphthyl, biphenylyl or anthracenyl. These cyclic systems may carry one or more identical or different substituents, for example, lower alkyl groups such as methyl, halogenated alkyl groups such as trifluoromethyl, lower alkoxy groups such as methoxy, or lower alkylthio(alkanesulfanyl) or alkanesulfonyl groups such as methylthio or ethanesulfonyl. The term substituted phenyl should be understood as referring to, in particular, groups such as fluorophenyl, methoxyphenyl, tolyl or trifluoromethylphenyl, with the substituents preferably being in the para position. Correspondingly, the term arylalkyl should be understood as referring to the groups formed from lower alkyl groups, in particular $C_{1-6}$-alkyl, by a hydrogen atom being replaced by one of the above-defined aryl groups, for example, benzyl or phenylethyl.

The 2,3-dichloropyridines (II) serving as the starting material either are known compounds or can be prepared in a manner similar to that for known compounds. [See, e.g., L. A. Paquette, *Encyclopedia of Reagents for Organic Synthesis*, John Wiley & Sons, New York, (1995), and Swiss Published Patent Application No. 664,754].

2,3-dichloro-5-(methoxymethyl)pyridine is novel and likewise forms part of the subject matter of the present invention.

Preferentially, methyl or ethyl esters are prepared (R=Me, Et) according to the novel method, by employing methanol or ethanol as the alcohol (III).

Likewise, preferred is the preparation of pyridine-2,3-dicarboxylic acid esters (I) which are unsubstituted in positions 4 and 6 of the pyridine ring ($R^1=R^3=H$).

Particularly preferred is the preparation of pyridine-2,3-dicarboxylic acid esters (I) which, in position 5 of the pyridine ring ($R^2$), carry hydrogen, a ($C_{1-4}$alkoxy)carbonyl group or a ($C_{1-4}$-alkoxy)methyl group.

The catalytically active palladium-diphosphine complex is advantageously formed in situ, palladium in finely disperse elemental form (e.g., palladium on activated carbon), a Pd(II) salt (e.g., the chloride or the acetate) or a suitable Pd(II) complex [e.g., dichloro-bis(triphenylphosphine)palladium(II)] being reacted with the diphosphine. Particularly preferred are palladium(II) acetate and dichloro-bis(triphenylphosphine)palladium(II). The palladium is preferably employed in an amount of from 0.02 to 5 mol percent of Pd(II) or from 0.5 to 5 mol percent of Pd(0) (as Pd/C), in each case based on the halogen compound (II). The diphosphine is advantageously employed in excess (based on Pd), preferably in an amount of from 0.2 to 10 mol percent, likewise based on the halogen compound (II).

The alcohol (III) may also serve as a solvent at the same time. If required, an additional solvent can be used. Possible additional solvents include both relatively nonpolar ones, for example, toluene or xylene, and polar ones, for example, acetonitrile, tetrahydrofuran or N,N-dimethylacetamide.

The base used is preferably an alkali metal acetate. Particularly preferred are sodium acetate and potassium acetate.

The reaction temperature preferably is from 80° to 250° C. The carbon monoxide pressure preferably is from 1 to 50 bar.

The reaction time depends, inter alia, on the temperature, the reactivity of the compounds used and the concentration conditions, and typically is in the range of a few hours. Since the two chlorine atoms of the dichloropyridine (II) are substituted successively and excessively long reactions times may give rise to secondary reactions, the progress of the reaction is advantageously monitored by means of a suitable analytical method (e.g., GC) and the reaction is terminated once the maximum product concentration has been reached.

DETAILED DESCRIPTION OF THE INVENTION

The following examples illustrate the implementation of the novel method.

EXAMPLE 1

Diethyl pyridine-2,3-dicarboxylate (I, R=Et, and $R^1=R^2=R^3=H$)

A metal autoclave was charged with 1.52 g (10 mmol) of 2,3-dichloropyridine (Fluka), 166 mg (0.3 mmol) of 1,1'-bis (diphenylphosphino)ferrocene, 22.4 mg (0.1 mmol) of palladium(II) acetate, 1.72 g (21 mmol) of sodium acetate and 25 ml of ethanol. The autoclave was repeatedly purged with carbon monoxide, the carbon monoxide pressure then being raised to 15 bar and the reaction mixture being heated to 135° C. (internal temperature) for 2.5 hours. The reaction mixture was then concentrated in vacuo and the residue was chromatographed on silica gel 60 with hexane/ethyl acetate (3:1). The yield of the product was 0.945 g (85 percent) of a colorless oil. Other data concerning the product was:

| | |
|---|---|
| $^1$H NMR(CDCl$_3$)δ = | 8.75(d, 1H); 8.19(d, 1H); 7.47(dd, 1H); 4.48(q, 2H); 4.39(q, 2H); 1.44(t, 3H); 1.39(t, 3H). |
| MS(m/z): | 223(M$^+$), 179; 150; 122; 107; 79. |

EXAMPLE 2

Trimethyl pyridine-2,3,5-tricarboxylate (I, R=Me, $R^1=R^3=H$, and $R^2=COOMe$)

In a manner similar to Example 1, 2.06 g (10 mmol) of methyl 5,6-dichloronicotinate (II, $R^1=R^3=H$, and $R^2=COOMe$), 128 mg (0.3 mmol) of 1,4-bis(diphenylphosphino)butane, 14.0 mg (20 µmol) of dichlorobis(triphenylphosphine)palladium(II) and 2.46 mg (30 mmol) of sodium acetate were reacted in 25 ml of methanol at 155° C. (bath temperature) and a CO pressure of 15 bar for 6 hours. GC analysis of the reaction mixture indicated a yield of 77 percent with a conversion ratio of 100 percent. The isolated yield of the product was 800 mg (50 percent) of yellow oil. Other data concerning the product was:

| | |
|---|---|
| $^1$H NMR(CDCl$_3$)δ = | 9.31(s, 1H); 8.78(s, 1H); 4.01(s, 3H); 4.00(s, 3H); 3.97(s, 3H). |
| MS(m/z): | 253(M$^+$), 223; 222; 195; 194; 165; 137. |

EXAMPLE 3

2,3-dichloro-5-(methoxymethyl)pyridine (II, $R^1$, $=R^3=H$, and $R^2=CH_2OMe$)

Under argon, 4.14 g (23 mmol) of sodium methylate (30 percent strength solution in methanol) was added dropwise at room temperature over a period of 5 minutes to a solution of 4.11 g (20.9 mmol) of 2,3-dichloro-5-(chloromethyl) pyridine [prepared from 2,3-dichloro-5-(hydroxymethyl)pyridine by reaction with thionyl chloride] in 40 ml of methanol. The reaction mixture was then heated to 60° C. for 3 hours. After the end of the reaction the solvent was distilled off, the residue was admixed with 100 ml of water and extracted with dichloromethane (3×75 ml). The organic phase was dried over magnesium sulfate and boiled down. The yield of the product was 4.06 g (90.4 percent) of yellow oil, content (GC) 90.8 percent. To analyze the product, it was chromatographed on silica gel with hexane/ethyl acetate (3:1).

| | |
|---|---|
| $^1$H NMR(CDCl$_3$)δ = | 8.25(s, 1H); 7.78(s, 1H); 4.46(s, 2H); 3.43(s, 3H). |
| MS(m/z): | 192(M$^+$), 176; 161; 148; 124; 112. |

EXAMPLE 4

Dimethyl 5-(methoxymethyl)pyridine-2,3-dicarboxylate (I, R=Me, R$^1$=R$^3$=H, and R$^2$=CH$_2$OMe)

In a manner similar to Example 1, 1.92 g (10 mmol) of 2,3-dichloro-5(methoxymethyl)pyridine (prepared in accordance with Example 3), 166 mg (0.3 mmol) of 1,1'-bis(diphenylphosphino)ferrocene, 14 mg (20 μmol) of dichlorobis(triphenylphosphine)palladium(II) and 2.46 g (30 mmol) of sodium acetate were reacted in 25 ml of methanol at 160° C. (bath temperature) and a CO pressure of 15 bar for 24 hours. GC analysis of the reaction mixture indicated a yield of 83 percent with a conversion ratio of 100 percent. The isolated yield of the product was 500 mg (41 percent) of yellow oil, content (GC) 97 percent. Other data concerning the product was:

| | |
|---|---|
| $^1$H NMR(CDCl$_3$)δ = | 8.70(s, 1H); 8.15(s, 1H); 4.57(s, 2H); 4.00(s, 3H); 3.92(s, 3H); 3.43(s, 3H). |
| MS(m/z): | 239(M$^+$), 209; 181; 151; 123. |

EXAMPLE 5

Dimethyl 5-(methoxymethyl)pyridine-2,3-dicarboxylate (I, R=Me, R$^1$=R$^3$=H, and R$^2$=CH$_2$OMe)

The same procedure was followed as described in Example 4, except that the reaction temperature was raised to 180° C. (bath temperature) and the reaction time was reduced to 4 hours. GC analysis of the reaction mixture indicated a yield of 79 percent with a conversion ratio of 100 percent. The isolated yield of the product was 750 mg (58 percent) of yellow oil, content (GC) 92.4 percent.

EXAMPLE 6

Dimethyl 5-(methoxymethyl)pyridine-2,3-dicarboxylate (I, R=Me, R$^1$=R$^3$=H, and R$^2$=CH$_2$OMe)

The same procedure was followed as described in Example 4, except that 4.4 mg (20 μmol) of palladium(II) acetate was used instead of dichlorobis(triphenylphosphine) palladium(II). The reaction temperature was 160° to 170° C. (bath temperature), and the reaction time was 5 hours. GC analysis of the reaction mixture indicated a yield of 90 percent with a conversion ratio of 100 percent. The isolated yield of the product was 740 mg (61 percent) of yellow oil, content (GC) 100 percent.

EXAMPLE 7

Dimethyl 5-(methoxymethyl)pyridine-2,3-dicarboxylate (I, R=Me, R$^1$=R$^3$=H, and R$^2$=CH$_2$OMe)

The same procedure was followed as described in Example 6, except that 2.94 g (30 mmol) of potassium acetate was used instead of sodium acetate. The reaction temperature was 170° C. (bath temperature), and the reaction time was 3 hours. GC analysis of the reaction mixture indicated a yield of 90 percent with a conversion ratio of 100 percent.

EXAMPLE 8

Diethyl 5-(methoxymethyl)pyridine-2,3-dicarboxylate (I, R=Et, R$^1$=R$^3$=H, and R$^2$=CH$_2$OMe)

In a manner similar to Example 4, 1.92 g (19 mmol) of 2,3-dichloro-5(methoxymethyl)pyridine, 166 mg (0.3 mmol) of 1,1'-bis(diphenylphosphino)ferrocene, 14.0 mg (20 μmol) of dichlorobis(triphenylphosphine)palladium(II) and 2.46 g (30 mmol) of sodium acetate were reacted in 25 ml of ethanol at 175° C. (bath temperature) and a CO pressure of 15 bar for 4 hours. GC analysis of the reaction mixture indicated a yield of 79 percent with a conversion ratio of 100 percent. The isolated yield of the product was 920 mg (67 percent) of yellow oil, content (GC) 98.1 percent. Other data concerning the product was:

| | |
|---|---|
| $^1$H NMR(CDCl$_3$)δ = | 8.70(s, 1H); 8.15(s, 1H); 4.55(s, 2H); 4.46(q, 2H); 4.40(q, 2H); 3.44(s, 3H); 1.42(t, 3H); 1.38(t, 3H). |
| MS(m/z): | 267(M$^+$), 236; 223; 194; 151; 123. |

EXAMPLE 9

Diethyl 5-(methoxymethyl)pyridine-2,3-dicarboxylate (I, R=Et, R$^1$=R$^3$=H, and R$^2$=CH$_2$OMe)

The same procedure was followed as described in Example 8, except that 4.4 mg (20 μmol) of palladium(II) acetate was used instead of dichlorobis(triphenylphosphine) palladium(II) and the amount of sodium acetate was reduced to 1.72 g (21 mmol). The reaction temperature was 155° C. (internal temperature), and the reaction time was 2 hours. GC analysis of the reaction mixture indicated a yield of 88 percent with a conversion ratio of 100 percent. The isolated yield of the product was 950 mg (67 percent) of yellow oil, content (GC) 94 percent.

EXAMPLE 10

Diethyl 5-(methoxymethyl)pyridine-2,3-dicarboxylate (I, R=Et, $R^1=R^3$=H, and $R^2=CH_2OMe$)

The same procedure was followed as described in Example 9, except that the reaction temperature was 145° C. (internal temperature) and the reaction time was 5 hours. GC analysis of the reaction mixture indicated a yield of 95 percent with a conversion ratio of 100 percent. The isolated yield of the product was 1100 mg (78.7 percent) of yellow oil, content (GC) 95.6 percent.

EXAMPLE 11

Diethyl 5-(methoxymethyl)pyridine-2,3-dicarboxylate (I, R=Et, $R^1=R^3$=H, and $R^2=CH_2OMe$)

The same procedure was followed as described in Example 9, except that 11 mg (50 μmol) of palladium(II) acetate was used. GC analysis of the reaction mixture indicated a yield of 98 percent with a conversion ratio of 100 percent. The isolated yield of the product was 1260 mg (90 percent) of yellow oil, content (GC) 95.4 percent.

EXAMPLE 12

Diethyl 5-trifluoromethylpyridine-2,3-dicarboxylate (I, R=Et, $R^1=R^3$=H, $R^2=CF_3$)

A Teflon®-lined 100 ml stainless steel autoclave equipped with a magnetic stirring bar was charged with 20 ml of ethanol, 1.70 g (20 mmol) of sodium acetate, 2.16 g (10 mmol) of 2,3-dichloro-5-trifluoromethylpyridine, 166 mg (0.3 mmol) of 1,1'-bis(diphenylphosphino)ferrocene and 12 mg (0.05 mmol) of palladium(II) acetate. The autoclave was purged with carbon monoxide and the carbon monoxide pressure adjusted to 15 bar. The reaction mixture was then heated to 150° C. (jacket temperature) and the reaction was carried out with stirring. After 2 hours, the reaction mixture was cooled to room temperature and filtered through Celite®. The mixture was concentrated in vacuo and the residue chromatographed on silica gel with hexane/ethyl acetate (4:1), affording 2.68 g (92 percent) of a colorless oil, b.p. (0.02 mm Hg): 80° C. Other data concerning the product was:

| | |
|---|---|
| $^1$H NMR(CDCl$_3$)δ = | 9.00(s, 1H); 8.47(s, 1H); 4.50(q, 2H); 4.42(q, 2H) 1.43(t,3H); 1.40(t,3H). |
| MS(m/z): | 292; 291(M$^+$); 246; 218; 174; 147. |

What is claimed is:

1. A method for preparing a pyridine-2,3-dicarboxylic acid ester of formula:

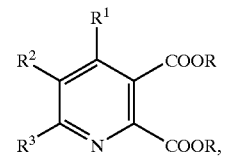

wherein R is $C_{1-6}$-alkyl, $C_{3-6}$-cycloalkyl, aryl or arylalkyl, and $R^1$ to $R^3$, independently of one another, is hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl, comprising reacting a 2,3-dichloropyridine of formula:

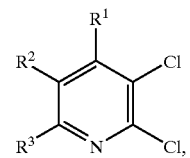

wherein $R^1$ and $R^3$ are each defined as above, with carbon monoxide and an alcohol of formula:

wherein R is defined as above, in the presence of (i) a catalytically active complex of palladium with a diphosphine of formula:

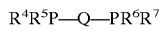

wherein $R^4$ to $R^7$, independently of one another, is phenyl, substituted phenyl, $C_{1-6}$-alkyl or $C_{3-6}$-cycloalkyl, and Q is a 1,1'-ferrocenediyl group, and (ii) a base that is selected from the group consisting of alkali metal salts of lower carboxylic acids, alkaline earth metal salts of lower carboxylic acids, alkali metal hydrogen carbonates, alkaline earth metal hydrogen carbonates, alkali metal (di)hydrogen phosphates and alkaline earth metal (di)hydrogen phosphates.

2. The method according to claim 1, wherein R is methyl or ethyl.

3. The method according to claim 2, wherein $R^1$ and $R^3$ are hydrogen.

4. The method according to claim 2, wherein $R^2$ is hydrogen, ($C_{1-4}$-alkoxy)carbonyl or ($C_{1-4}$-alkoxy)methyl.

5. The method according to claim 4, wherein the catalytically active palladium complex is formed in situ from the diphosphine (IV) and palladium(II) acetate or dichlorobis(triphenylphosphine)palladium(II).

6. The method according to claim 5, wherein the base employed is an alkali metal acetate.

7. The method according to claim 6, wherein the base employed is sodium acetate or potassium acetate.

8. The method according to claim 1, wherein $R^1$ and $R^3$ are hydrogen.

9. The method according to claim 1, wherein $R^2$ is hydrogen, ($C_{1-4}$-alkoxy)carbonyl or ($C_{1-4}$-alkoxy)methyl.

10. The method according to claim 1, wherein the catalytically active palladium complex is formed in situ from the diphosphine (IV) and palladium(II) acetate or dichlorobis(triphenylphosphine)palladium(II).

11. The method according to claim 1, wherein the base employed is a alkali metal acetate.

12. The method according to claim 1, wherein the base employed is sodium acetate or potassium acetate.

13. A method for preparing a pyridine-2,3-dicarboxylic acid ester of formula:

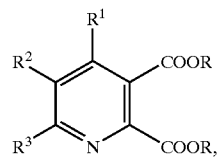

I wherein R is $C_{1-6}$-alkyl, $C_{3-6}$-cycloalkyl, aryl or aylalkyl, and $R^1$ to $R^3$, independently of one another, is hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl, comprising reacting a 2,3-dichloropyridine of formula:

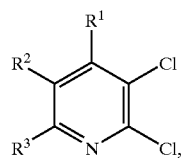

II wherein $R^1$ to $R^3$ are each as defined above, with carbon monoxide and an alcohol of formula:

wherein R is defined as above, in the presence of (I) a catalytically active complex of palladium with a diphosphine of formula:

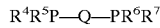

wherein $R^4$ to $R^7$, independently of one another, is phenyl, substituted phenyl, $C_{1-6}$-alkyl or $C_{3-6}$-cycloalkyl, and Q is a group of the formula —$[CH_2]_n$—, wherein n is 3 or 4, and (ii) a base that is selected from the group consisting of alkali metal salts of lower carboxylic acids, alkaline earth metal salts of lower carboxylic acids, alkali metal hydrogen carbonates, alkaline earth metal hydrogen carbonates, alkali metal (di)hydrogen phosphates and alkaline earth metal (di)hydrogen phosphates.

14. The method according to claim 13, wherein R is methyl or ethyl.

15. The method according to claim 14, wherein $R^1$ and $R^3$ are hydrogen.

16. The method according to claim 15, wherein $R^2$ is hydrogen, ($C_{1-4}$-alkoxy)carbonyl or ($C_{1-4}$-alkoxy)methyl.

17. The method according to claim 16, wherein the catalytically active palladium complex is formed in situ from the diphosphine (IV) and palladium(II) acetate or dichlorobis(triphenylphosphine)palladium(II).

18. The method according to claim 17, wherein the base employed is an alkali metal acetate.

19. The method according to claim 18, wherein the base employed is sodium acetate or potassium acetate.

20. The method according to claim 13, wherein $R^1$ and $R^3$ are hydrogen.

21. The method according to claim 13, wherein $R^2$ is hydrogen, ($C_{1-4}$-alkoxy)carbonyl or ($C_{1-4}$-alkoxy)methyl.

22. The method according to claim 13, wherein the catalytically active palladium complex is formed in situ from the diphosphine (IV) and palladium(II) acetate or dichlorobis(triphenylphosphine)palladium(II).

23. The method according to claim 13, wherein the base employed is an alkali metal acetate.

24. The method according to claim 23, wherein the base employed is sodium acetate or potassium acetate.

25. The method according to claim 1, wherein the base has a pK of 4 to 9.

26. The method according to claim 1, wherein a solvent, other than said alcohol (III), is present.

27. The method according to claim 13, wherein the base has a pK of 4 to 9.

28. The method according to claim 13, wherein a solvent, other than said alcohol (III), is present.

\* \* \* \* \*